United States Patent [19]

LaBella et al.

[11] Patent Number: 5,270,457
[45] Date of Patent: Dec. 14, 1993

[54] CARDIAC STERIOD GLYCOSIDES

[75] Inventors: Frank S. LaBella, Oakbank; John F. Templeton; Yangzhi Ling, both of Winnipeg, all of Canada

[73] Assignee: University of Manitoba, Winnipeg, Canada

[21] Appl. No.: 897,422

[22] Filed: Jun. 12, 1992

[51] Int. Cl.$^5$ .................... C07J 41/00; A61K 31/705
[52] U.S. Cl. ........................ 536/5; 540/106; 552/557; 552/582
[58] Field of Search ............ 514/26, 182; 536/5; 540/106; 552/557, 582

[56] References Cited

U.S. PATENT DOCUMENTS 4,882,315 11/1989 Chiodini et al. ............ 514/26
5,144,017 9/1992 LaBella et al. .............. 536/5

OTHER PUBLICATIONS

Lucas et al; J. Am. Chem. Soc. 82:5688–5693 (1960).
Katzung et al; Experientia 26(11):1189–91 (1970).
Eberlein et al; Chem. Ber. 107:1275–1284 (1974).
Rohrer et al; J. Am. Chem. Soc. 98(20):6308–6312 (1976).
Kim et al; Molecular Pharmacology 18:402–405 (1980).
Brown et al; Arznei M. Forsch./Drug Res. 31(II), No. 7:1059–1064 (1981).
Templeton et al; Can. J. Physiol. Pharmacol. 66:1420–1424 (1988).

Primary Examiner—Nancy S. Husarik
Attorney, Agent, or Firm—Sim & McBurney

[57] ABSTRACT

14$\beta$-hydroxy-3$\beta$-($\alpha$-L-rhamnopyranosyl)- and-tridigitoxide-oxy-20-nitro-21-nor-5$\beta$,14$\beta$-pregnanes exhibit unexpectedly high cardiac potency with tolerance to high dosage levels.

2 Claims, 1 Drawing Sheet

CARDIAC STERIOD GLYCOSIDES

FIELD OF INVENTION

The present invention relates to novel cardiac steroids having a surprising cardiac binding potency.

BACKGROUND OF THE INVENTION

In our copending U.S. patent application Ser. No. 462,234 filed Jan. 9, 1990 (now U.S. Pat. No. 5,144,017), we have described certain C3-glycoside derivatives of certain 14β-hydroxypregnanes, their cardiac stimulant properties and potential as digoxin substitutes. In our copending U.S. patent application Ser. No. 633,274 filed Dec. 24, 1990(now abandoned), we describe the potassium-sparing diuretic effect of digitaloid pregnane glycoside derivatives.

SUMMARY OF INVENTION

In this invention, we have now surprisingly found that certain specific C3-glycoside derivatives of certain 14β-hydroxypregnanes exhibit a surprisingly-high potency, having regard to the potency data obtained for analog compounds, and a potency comparable to the natural cardiac glycosides, like digoxin.

The compound is 14B-hydroxy-3β-(α-L-rhamnopyranosyl)oxy-20-nitro-21-nor-5β,14β-pregnane, i.e. the compound of the formula:

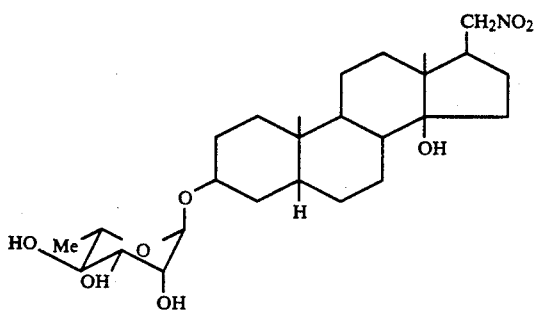

as well as its trisdigitoxide analog.

The rhamnopyranosyl compound of the above formation exhibits a potency (IC$_{50}$) in an $^3$H-ouabain radioligand binding assay (RBA) of 11 nM, in comparison to an IC$_{50}$ value for the corresponding —NH$_2$ analog of 60 nm. The trisdigitoxoside compound corresponding to the rhamnopyranosyl compound of the above formation also exhibits a high degree of potency of 60 nM.

GENERAL DESCRIPTION OF INVENTION

Figure 1:
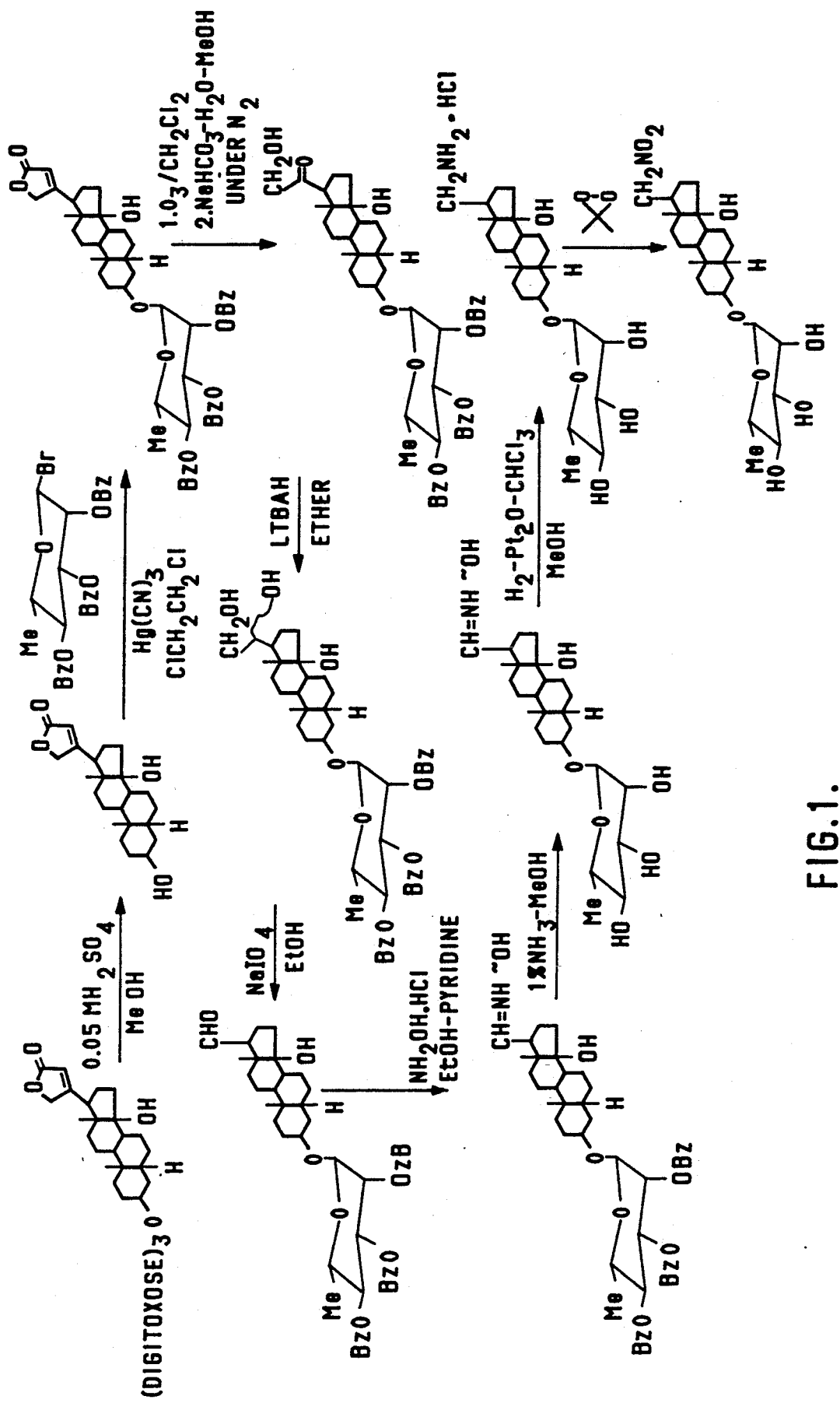
FIG. 1 is a schematic representation of the procedure for obtaining the novel compounds herein.

As noted above, the present invention relates to specific compounds which exhibit unexpectedly high potency in a $^3$H-ouabain radioligand binding assay (RBA). The potency of steroids to displace the labelled cardiac glycoside (i.e. ouabain) in the assay parallel their biological activity, that is their cardiac glycoside-like activity, in their ability to inhibit Na/K-ATPase and elicit characteristic cellular response.

The unexpectedly high potency observed for the compounds of the invention is comparable to that for digoxin. The compounds also exhibit enhanced cardiac contractility. Unlike digoxin, however, an animal administered with the compounds of the present invention exhibits a tolerance to higher dosage levels. A synthesis scheme for the α-L-rhamnopyranosyl novel compound is shown in FIG. 1. The trisdigitoxide may be made in the same way.

EXAMPLES

Example 1

14-Hydroxy-3β-(α-L-rhamnopyranosyl)oxy-20-amino-21-nor-5β14β-pregnane hydrochloride 14-Hydroxy-3β-(α-L-rhamnopyranosyl)oxy-21-nor-5β,- 14β-pregnane 20 (E/Z)-oxime (50 mg) and platinum oxide (25 mg) in methanol (5 ml) containing chloroform (0.3 ml) was shaken in a hydrogen atmosphere for 20 hr when no starting remained on TLC (CHCl$_3$:CH$_3$OH:NHEt$_2$; 10:1:0.75). The reaction mixture was filtered (Celite), evaporated at room temperature to give on recrystallization from ether, the 20-amine hydrochloride (33 mg) m.p. 217°-218° C. $^1$H NMR (CD$_3$OD) δ: 1.00 (10& 13-Me), 1.27d, J 6.2 Hz (5'-Me), 3.06m (20-H$_2$), 3.40t, J 9.4 Hz(4,H), 3.70m (3' and 5'H), 3.80 dd, J 1.6,3.2 Hz (2'H), 3.98 br s (3αH), 4.80 d, J 3.0 Hz (1'H) ppm. —C NMR (CD$_3$OD) δ: 30.87$^a$(1), 27.50$^b$(2), 73.59(3), 31.64$^a$(4), 38.16(5), 27.80$^b$(6), 21.88$^c$(7), 42.01(8), 36.82(9), 36.30(10), 22.35$^c$(11), 39.81(12), ca. 50(13), 86.32(14), 32.64(15), 24.87(16), 49.00(17), 15.15(18), 24.36(19), 43.53(20), 99.85(1,), 72.53(2'), 72.93(3'), 74.07(4'), 70.02(5'), 17.97(6') ppm; a,b,c Indicate interchangeable values.

Anal. C, 60.67, H, 9.26; N, 2.68; Cl, 6.91, C$_{26}$H$_{46}$O$_6$NCl.0.5 H$_2$O requires C, 60.86; H, 9.23; N, 2.73; Cl, 6.91%.

IC$_{50}$ 60 nM

Example 2

14-Hydroxy-3β-(α-L-rhamnopyranosyl)oxy-20-nitro-21-nor-5β,14β-pregnane

14-Hydroxy-3β-(α-L-rhamnopyranosyl)oxy-20-amino-21-nor-5β,14β-pregnane hydrochloride (60 mg), prepared as described in Example 1 was dissolved in methanol (1 ml) and a freshly prepared solution of dimethyldioxirane in acetone (8 ml, ca. 0.1M) was added at room temperature [W. Adam, Y. Y. Chan, D. Cremer, J. Gause, D. Scheutzow and M. Schindler, J. Org. Chem., 52, 2800 (1987); R. W. Murray, S. N. Rajadhyaksha and L. Mohan, J. Org. Chem., 54, 5783 (1989).] After 30 min no starting material remained by TLC (acetone:hexane,1:1) and the solvents were evaporated and the residue flash-chromatographed (acetone-hexane, 1:1) to give the nitro compound (42 mg, 70%) m.p. 265°-268° C.

$^1$H NMR (CDCl$_3$) δ: 0.89 (13-Me), 0.92 (10-Me), 1.27d, J 6.2Hz (5'-Me), 2.43m (17αor 16βH), 3.40, t J 9.4 Hz (4'H), 3.70m (3'& 5'H), 3.81 dd, J 1.6, 3.1 Hz (2'H), 3.97 br s (3αH), 4.60m (1'H & 20 CH$_2$) ppm. $^{13}$C NMR δ: 30.03$^a$(1), 26.96$^b$(2), 73.20 (3), 30.73$^a$(4), 37.24 (5), 26.68$^b$(6), 21.40$^c$(7), 41.25(8), 35.89(9), 35.49(10), 20.91$^c$(11), 38.52(12), ~50 (13), 85.90(14), 31.51(15), 25.13(16), 48.27(17) 14.09(18), 23.66(19), 80.78(20), 98.85(1'), 71.65(2'), 71.95(3'), 72.61(4'), 69.05(5'), 17.19(6') ppm; $^{a-c}$ Indicate interchangeable values.

Anal. C, 60.53; H, 8.69; N, 2.68, C$_{26}$H$_{43}$O$_8$N.H$_2$O requires C, 60.58; H, 8.73; N, 2.76%. IC$_{50}$ 11nm. This potency is significantly greater than exhibited by the corresponding amino derivative (Example 1) and tridigitoxosyl derivative (Example 4).

Example 3

14-Hydroxy-3β-(tris-β-D-digitoxosyl)oxy-20-amine-21-nor-5β,14β-pregnane

The etianaldehyde (300 mg) derived from digitoxin [W. Eberlein, W. Diederen, J. Heider and W. Kobinger, Chem. Abst., (German Patent 20 52 634.5), 77, 62237 (1972)] was dissolved in a mixture of 95% ethanol (20 ml) to which hydroxylamine hydrochloride (600 mg) and a solution of sodium acetate (430 mg) in water (5 ml) and pyridine (7.5 ml) had been added. After 2 hrs reflux the TLC (4.5% methanol-dichloromethane) indicated no starting material and two products (cis and trans oximes) had formed. Dilution with water followed by dichloromethane extraction gave the crude product which was dissolved in n-propanol (20 ml) and brought to reflux under argon. Sodium metal (1.2 g) was added portionwise over 2.5 hrs when TLC (10%-methanol-dichloromethane) indicated no starting material and one product. Extraction with dichloromethane, which was then thoroughly washed with water, gave on two crystallizations from methanol-ether the 20-amine (86 mg), m.p. 239°–243° C. $^1$H NMR (CD$_3$OD: CDCl$_3$; 1:1) δ: 0.94 and 0.95 (10 and 13-Me), 2.70s, 2.72s ($J_{AB}=J_{AX}=J_{BX}=0$) (20-H$_2$), 4.03 br s (3αH), and appropriate signals for the tris-B-D-digitoxoside. $^{13}$C NMR (CD$_3$OD:CDCl$_3$; 1:1) δ: 30.89(1), 27.12(2), 73.83(3), 30.46(4), 37.28(5), 27.36(6), 21.54(7), 41.29(8), 36.18(9), 35.77(10), 22.02(11), 40.41(12), ~50(13), 84.76(14), 33.11(15), 23.95(16), 52.37(17), 15.33(18), 24.12(19), 42.51(20).

Anal. C, 64.02; H, 9.35; N, 1.94, C$_{38}$H$_{65}$O$_{11}$N requires C, 64.11; H, 9.20; N, 1.97%. IC$_{50}$ 400 nM

Example 4

14-Hydroxy-3 β-(tris-β-D-digitoxosyl)oxy-20-nitro-21-nor-5β,14β-pregnane

14-Hydroxy-3B-(tris-β-D-digitoxosyl)oxy-20-nitro-21-nor-5β,14β-pregnane (142 mg), prepared as described in Example 3), in dichloromethane (50 ml) was cooled to −78° C. in a dry-ice acetone bath and an excess of ozone passed through the solution for 2.5 hrs. Excess ozone was removed with a stream of nitrogen. The solvent was evaporated to give a residue which was passed through a column of silica (flask chromatography). Elution with 3% methanol-dichloromethane gave, on recrystallization from ether, the 20-nitro derivative (50 mg) m.p. 246°–249° C. $^1$H NMR (CD$_3$OD:CDCl$_3$; 1:1)δ: 0.94 and 0.95 (10 and 13-Me), 2.44m (16β or 17αH), 4.04 br s (3αH), 4.56s, 4.59s, $J_{AB}=J_{AX}=J_{BX}=0$ (20-H$_2$). $^{13}$C NMR (CO$_3$OD: CDCl$_3$; 1:1) δ: 30.86(1), 27.10(2), 73.51(3), 30.49(4), 37.2S(5), 27.26(6), 21.27(7), 41.58(S), 36.30(9), 35.83(10), 21.76(11), 38.91(12), ~50(13), 86.26 (14), 32.02(15), 25.55(16), 54.13(17), 14.65(18), 24.05(19), 81.25(20).

Anal C, 61.40; H, 8.61; N, 1.65, C$_{38}$H$_{63}$O$_{13}$N requires C, 61.52; H, 8.56; N, 1.89%. IC$_{50}$ 60nM

SUMMARY OF DISCLOSURE

In summary of this disclosure, the present invention provides novel 14β-hydroxypregnane derivatives exhibiting high cardiac potency. Modifications are possible within the scope of this invention.

What we claim is:

1. A 14 β-hydroxypregnane compound of the formula:

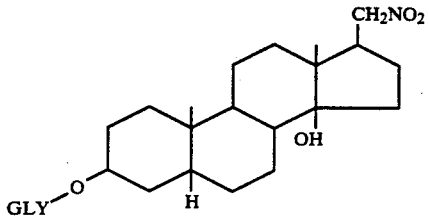

wherein GLY is α-L-rhamnopyranosyl or trisidigitoxide.

2. The compound of claim 1 wherein GLY is α-L-rhamnopyranosyl.

* * * * *